United States Patent
Ali

(10) Patent No.: US 8,653,315 B2
(45) Date of Patent: Feb. 18, 2014

(54) MULTIPLE ZEOLITE CATALYST AND METHOD OF USING THE SAME FOR TOLUENE DISPROPORTIONATION

(71) Applicant: King Fahd University of Petroleum and Minerals, Dhahran (SA)

(72) Inventor: Mohammad A. Ashraf Ali, Dhahran (SA)

(73) Assignee: King Fahd University of Petroleum and Minerals, Dhahran (SA)

(*) Notice: Subject to any disclaimer, the term of this patent is extended or adjusted under 35 U.S.C. 154(b) by 0 days.

(21) Appl. No.: 13/687,982

(22) Filed: Nov. 28, 2012

(65) Prior Publication Data

US 2013/0090507 A1   Apr. 11, 2013

Related U.S. Application Data

(63) Continuation-in-part of application No. 12/219,927, filed on Jul. 30, 2008, now abandoned, and a continuation-in-part of application No. 13/353,085, filed on Jan. 18, 2012, now Pat. No. 8,329,973.

(51) Int. Cl.
*C07C 6/12* (2006.01)

(52) U.S. Cl.
USPC ........................................ 585/475

(58) Field of Classification Search
USPC ........................................ 585/475
See application file for complete search history.

(56) References Cited

U.S. PATENT DOCUMENTS

| | | |
|---|---|---|
| 3,790,471 A | 2/1974 | Argauer et al. |
| 3,855,328 A | 12/1974 | Hedge |
| 3,894,934 A | 7/1975 | Owen et al. |
| 3,928,174 A | 12/1975 | Bonacci et al. |
| 4,052,476 A | 10/1977 | Morrison |
| 4,116,814 A | 9/1978 | Zahner |
| 4,137,195 A | 1/1979 | Chu |
| 4,992,402 A | 2/1991 | Schweizer |
| 5,365,004 A | 11/1994 | Beck et al. |
| 5,367,099 A | 11/1994 | Beck et al. |

(Continued)

FOREIGN PATENT DOCUMENTS

| | | |
|---|---|---|
| EP | 0296582 A2 | 6/1988 |
| EP | 0923989 A3 | 3/2000 |

(Continued)

OTHER PUBLICATIONS

Huheey et al., *Inorganic Chemistry*, 4th ed., Harper Collins College Publishers, New York, 1993, pp. 745-748.

(Continued)

*Primary Examiner* — Thuan D Dang
(74) *Attorney, Agent, or Firm* — Richard C. Litman

(57) ABSTRACT

The multiple zeolite catalyst is a catalytic composition used to convert alkylaromatic hydrocarbons to BTX, particularly to commercially valuable xylenes. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VI of the Periodic Table of the Elements. The two zeolites have different physical and chemical characteristics, such as pore size and acidity. An exemplary catalyst includes mordenite, ZSM-5, and 3 wt % molybdenum. The multiple zeolite catalyst may further be used to convert toluene to mixed xylene isomers, particularly with a ZSM-5:mordenite ratio of 2:1 by weight.

8 Claims, 3 Drawing Sheets

(56) References Cited

U.S. PATENT DOCUMENTS

| | | |
|---|---|---|
| 5,705,726 A | 1/1998 | Abichandani et al. |
| 5,763,720 A | 6/1998 | Buchanan et al. |
| 5,773,676 A | 6/1998 | Drake et al. |
| 5,847,256 A | 12/1998 | Ichioka et al. |
| 5,866,744 A | 2/1999 | Wu et al. |
| 5,905,051 A | 5/1999 | Wu et al. |
| 5,942,651 A | 8/1999 | Beech, Jr. et al. |
| 6,037,294 A | 3/2000 | Drake et al. |
| 6,040,259 A | 3/2000 | Mohr et al. |
| 6,198,013 B1 | 3/2001 | Mohr et al. |
| 6,300,270 B1 | 10/2001 | Wu et al. |
| 6,323,381 B1 | 11/2001 | Nacamuli et al. |
| 6,417,421 B1 | 7/2002 | Yao |
| 6,462,247 B1 | 10/2002 | Kelly et al. |
| 6,504,073 B1 | 1/2003 | Ushio et al. |
| 6,504,074 B2 | 1/2003 | Verduijn et al. |
| 6,514,896 B1 | 2/2003 | Drake et al. |
| 6,541,408 B2 | 4/2003 | Chang et al. |
| 6,812,181 B2 | 11/2004 | van der Berge et al. |
| 6,855,854 B1 | 2/2005 | James, Jr. |
| 6,972,348 B2 | 12/2005 | Negiz et al. |
| 7,109,389 B2 | 9/2006 | Kong et al. |
| 7,148,391 B1 | 12/2006 | Buchanan et al. |
| 2001/0014645 A1 | 8/2001 | Ishikawa et al. |
| 2002/0082460 A1 | 6/2002 | Verduijn et al. |
| 2002/0091293 A1 | 7/2002 | Chang et al. |
| 2003/0092950 A1 | 5/2003 | Xiao et al. |
| 2005/0197518 A1 | 9/2005 | Miller et al. |
| 2005/0234279 A1 | 10/2005 | Serra et al. |
| 2006/0128555 A1 | 6/2006 | Shan et al. |

FOREIGN PATENT DOCUMENTS

| | | |
|---|---|---|
| EP | 55529 | 1/2003 |
| JP | 62-71546 | 4/1987 |
| JP | 09-038505 | 2/1997 |
| JP | 09-155198 | 6/1997 |
| WO | WO 9624568 A1 | 8/1996 |

OTHER PUBLICATIONS

Sherman, J.D., "Synthetic zeolites and other macroporous oxide molecular sieves," Proc. Natl. Acad. Sci. USA, vol. 96, (Mar. 1999) pp. 3471-3478 (p. 3471 only).

_US 8,653,315 B2_

MULTIPLE ZEOLITE CATALYST AND METHOD OF USING THE SAME FOR TOLUENE DISPROPORTIONATION

CROSS-REFERENCE TO RELATED APPLICATION

This application is a continuation-in-part of U.S. patent application Ser. No. 12/219,927, filed on Jul. 30, 2008, and of U.S. patent application Ser. No. 13/353,085, filed Jan. 18, 2012, which is a continuation of the Ser. No. 12/219,927 application.

BACKGROUND OF THE INVENTION

1. Field of the Invention

The present invention relates to catalysts used in petroleum refining, and particularly to a multiple zeolite catalyst and a method of using the same for toluene disproportionation.

2. Description of the Related Art

Aromatic hydrocarbons are the building blocks for many industrially important products. They are generally produced in a petrochemical complex. There are several commercial processes producing aromatics, especially xylene isomers, using a variety of reactions. Xylene isomers, including para-xylene, meta-xylene and ortho-xylene, are important intermediates, which find wide and varied application in chemical syntheses. Upon oxidation, p-xylene yields terephthalic acid, which is used in the manufacture of polyester plastics and synthetic textile fibers (such as Dacron), films (such as Mylar), and resins (such as polyethylene terephthalate, used in making plastic bottles). m-Xylene is used in the manufacture of plasticizers, azo dyes, wood preservers, etc. o-Xylene is feedstock for phthalic anhydride production, which is used to make polyester, alkyl resins, and PVC plasticizers.

Xylene isomer streams from catalytic reforming or other sources generally do not match demand proportions as chemical intermediates. p-Xylene, in particular, is a major chemical intermediate with rapidly growing demand, but amounts to only 20 to 25% of a typical $C_8$ aromatics stream. Among the aromatic hydrocarbons, the overall importance of the xylenes rivals that of benzene as a feedstock for industrial chemicals. The xylenes are produced from petroleum by the reforming of naphtha in insufficient volume that is difficult to meet the demand, and conversion of other hydrocarbons is necessary to increase the yield of xylenes.

A current objective of many aromatics production facilities is to increase the yield of xylenes by converting heavy aromatics, such as $C_9$, $C_{10}$ and $C_{11+}$, and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene, thus, is a favorable objective, and processes to convert $C_{9+}$ aromatics have been commercialized to obtain high xylene yields.

Aromatic hydrocarbon compounds contained in a gasoline base generally have higher octane values and are superior as a gasoline base because of their high calorific value. Among them, toluene and aromatic hydrocarbon compounds, those having eight carbon atoms especially, have higher octane values and driveability levels; thus, it is desirable to increase the volume of $C_8$ aromatic compounds in gasoline. In particular, methods of directly converting aromatic hydrocarbon compounds having nine or more carbon atoms in a gasoline fraction into toluene and aromatic hydrocarbon compounds having eight carbon atoms are significantly meaningful.

Reactions of aromatic hydrocarbon compounds to convert aromatic hydrocarbon compounds to compounds having a different number of carbon atoms include the transalkylation reaction and the disproportionation reaction. A transalkylation reaction is one in which an alkyl group, e.g., a methyl group, is detached from a first compound and then attached to a second compound. A disproportionation reaction is a reaction in which a single compound acts as both an oxidizing agent and a reducing agent.

A well-known process regarding these reactions is the manufacture of xylenes utilizing the disproportionation reaction of toluene, i.e., two molecules of toluene react to form one molecule of benzene and one molecule of xylene (by transfer of a methyl group from one molecule of toluene to the other, a transalkylation reaction). Transalkylation reactions, however, are not limited to the disproportionation of toluene. Other methods of increasing xylene yields operate through inducing transalkylation by adding aromatic hydrocarbon compounds having nine or more carbon atoms into the starting materials, resulting in such reactions as the addition of one mole of toluene to one mole of a $C_9$ aromatic hydrocarbon to produce two moles of xylene. Examples of such transalkylation reactions are illustrated in paragraphs [0009] through [0011] of U.S. Patent Publication 2005/0187518, which are hereby incorporated by reference.

Further, it is known to separate isomers through molecular sieves formed by zeolites. Zeolites are generally hydrated aluminum and calcium (or sodium) silicates that can be made or selected with a controlled porosity for catalytic cracking in petroleum refineries, and may be natural or synthetic. The pores may form sites for catalytic reactions to occur, and may also form channels that are selective for the passage of certain isomers to the exclusion of others. Zeolites may serve as Brönsted acids by hydrogen ion exchange by washing with acids, or as Lewis acids by heating to eliminate water from the Brönsted sites. For example, the zeolite ZSM-5 $(Na_3Al_3Si_{93}O_{192}.16H_2O)$ has a pore size that results in the formation of channels of such size and shape that it forms a selective sieve for xylene isomers. The alkylation of toluene by methanol will form a mixture of all three xylene isomers. p-Xylene will pass through the channels in ZSM-5 due to its linear configuration, while o-xylene and m-xylene will not pass through the pores, although they may subsequently rearrange to p-xylene under the acidic conditions in the pores and then pass through the sieve. See Huheey et al., _Inorganic Chemistry_, 4th ed., pp. 745-748.

The catalytic activity of zeolites can also be increased by addition of a metal catalyst that activates hydrogen by breaking up molecular hydrogen to atomic hydrogen on the surface of the metal for forming intermediates in transalkylation reactions.

Many types of supports and elements have been disclosed for use as catalysts in processes to convert heavier aromatics into xylenes. However, as the number of such supports and elements attests, none have been found entirely satisfactory. Hence, an improvement of even a few percentage points in conversion efficiency may be significant, particularly when practiced at high volumes on an industrial scale in oil refining facilities. Thus, a multiple zeolite catalyst and a method of using the same for toluene disproportionation solving the aforementioned problems is desired.

SUMMARY OF THE INVENTION

The multiple zeolite catalyst is a catalytic composition used to convert aromatic hydrocarbons, such as toluene, into xylene, benzene, toluene, xylene isomers and the like. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VI of the Periodic Table' of the Elements.

Preferably, the first zeolite has a greater acidity than the second zeolite, and the first zeolite has a higher overall concentration than that of the second zeolite in the multiple zeolite catalyst. Further, a concentration of ammonia-based acidity of the first zeolite is preferably greater than a concentration of ammonia-based acidity of the second zeolite. Similarly, a multipoint Brunauer-Emmett-Teller (BET) surface area of the first zeolite is preferably higher than a multipoint BET surface area of the second zeolite. The at least one metal component preferably forms between approximately 0.1% by weight and approximately 5.0% by weight of the multiple zeolite catalyst.

An exemplary catalyst includes a first zeolite comprising ZSM-5 and a second zeolite comprising mordenite, the at least one metal component being molybdenum or a compound thereof. In this exemplary catalyst, molybdenum forms about 3% by weight of the catalyst, and the mordenite has a silica-to-alumina molar ratio of about 240:1. Additionally, the ZSM-5 has a silica-to-alumina molar ratio of about 30:1.

The first zeolite preferably has a crystalline particulate size between approximately 0.45 microns and approximately 400 microns, where approximately 53.4% by volume of the first zeolite has a crystalline particulate size between approximately 1 micron and approximately 10 microns, and approximately 19.1% by volume of the first zeolite has a crystalline particulate size between approximately 10 microns and approximately 20 microns. The second zeolite preferably has a crystalline particulate size between approximately 0.45 microns and approximately 80 microns, where approximately 62.2% by volume of the second zeolite has a crystalline particulate size between approximately 1 micron and approximately 10 microns, and approximately 17.6% by volume of the second zeolite has a crystalline particulate size between approximately 10 microns and approximately 20 microns.

The multiple zeolite catalyst may further include an inorganic oxide binder, such as magnesia, zirconia, chromia, titania, boria, phosphate, zinc oxide, silica or, preferably, alumina.

The multiple zeolite catalyst may be used to perform toluene disproportionation, i.e., converting toluene into xylenes. The multiple zeolite catalyst contacts a toluene stream to perform the disproportionation. The disproportionation reaction preferably occurs at a temperature between approximately 200° C. and approximately 500° C. (more preferably, about 275° C. to 350° C., a pressure between 10-30 bar, and at a liquid hourly space velocity between approximately 1.0 $hr^{-1}$ and approximately 5.0 $hr^{-1}$ (more preferably, between 1.5 and 3.0 $hr^{-1}$, and the toluene stream preferably has a hydrogen to hydrocarbon ratio of about 2:1. The multiple zeolite catalyst acts as a solid acid catalyst in the toluene disproportionation reaction, thus producing toluene conversion and higher xylene yields at lower temperatures than in conventional toluene disproportionation processes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The multiple zeolite catalyst is a catalytic composition used to convert aromatic hydrocarbons into benzene-toluene-xylene (BTX) hydrocarbons, including commercially-valuable xylenes, and particularly for converting toluene into xylene isomers. The catalyst is formed by mixing at least two zeolites selected from mordenite, beta zeolite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41, and adding at least one metal component selected from Group VI of the Periodic Table of the Elements.

Preferably, the first zeolite has a greater acidity than the second zeolite, and the first zeolite preferably has a higher overall concentration than that of the second zeolite in the multiple zeolite catalyst. The amount of this first zeolite may range from between approximately 10 and 90 wt % of the total catalyst amount in the final dried and calcined form. Further, a concentration of ammonia-based acidity of the first zeolite is preferably greater than a concentration of ammonia-based acidity of the second zeolite. Similarly, a multipoint Brunauer-Emmett-Teller (BET) surface area of the first zeolite is preferably higher than a multipoint BET surface area of the second zeolite.

Figure 1A:
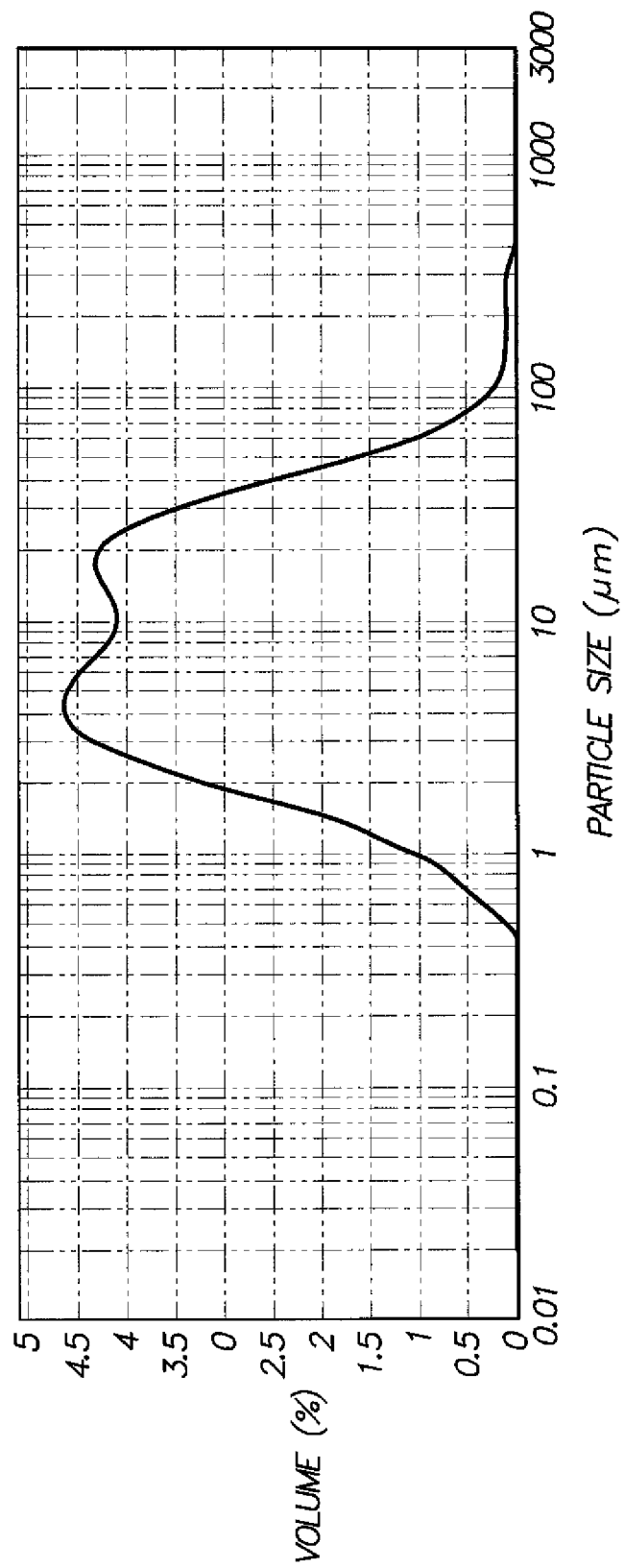
FIG. 1A illustrates particle analysis size data of a first zeolite of the multiple zeolite catalyst according to the present invention.
Figure 1B:
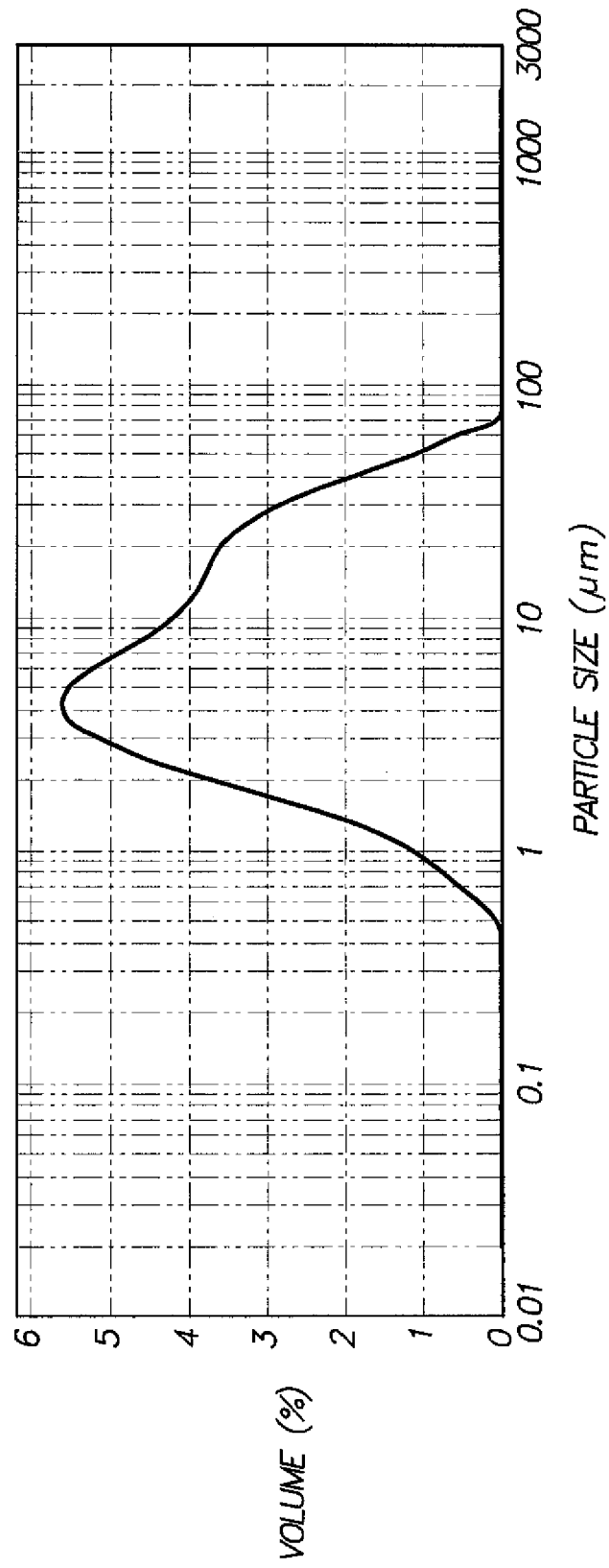
FIG. 1B illustrates particle analysis size data of a first zeolite of the multiple zeolite catalyst according to the present invention.

The metal component may be present in the final catalyst composite in any amount that is catalytically effective, generally comprising about 0.1 to about 5.0 wt % of the final catalyst calculated on an elemental basis. It should be understood that the at least one metal component may be any Group VI metal, such as chromium or tungsten, molybdenum being preferred. The metal component may exist within the final catalytic composite as a compound, such as an oxide, sulfide, or halide, in chemical combination with one or more of the other ingredients of the composite, or, preferably, as an elemental metal. Preferably, the pore size of the first zeolite is also selected so as to differ from that of the second zeolite. Additionally, although the first zeolite preferably has a higher overall concentration than that of the second zeolite in the multiple zeolite catalyst, the second zeolite may range from between approximately 10 and 90 wt % of the total catalyst amount in the final dried and calcined form. FIGS. 1A and 1B show particle size analysis results of the first and second zeolites, respectively.

The metal component may exist within the final catalytic composite as a compound, such as an oxide, sulfide, or halide, in chemical combination with one or more of the other ingredients of the composite, or, preferably, as an elemental metal. The metal component may be incorporated into the catalyst in any suitable manner, such as co-precipitation or co-gelation with the carrier material, ion exchange or impregnation. Impregnation using water-soluble compounds of the metal is preferred.

An exemplary catalyst includes a first zeolite formed from ZSM-5 and a second zeolite formed from mordenite, the at least one metal component being molybdenum or a compound thereof. In this exemplary catalyst, approximately 3% by weight of the catalyst consists of the at least one metal component, and the mordenite has a silica to alumina molar ratio of approximately 240:1. Additionally, the ZSM-5 has a silica to alumina molar ratio of approximately 30:1.

The inventors have found that in use, this embodiment of the multiple zeolite catalyst is optimally configured for transalkylation of C9+ alkylaromatics to BTX when the ratio of mordenite to ZSM-5 is about 2:1 by weight, and is optimally configured for conversion of C7 alkylaromatics to BTX, particularly xylenes, when the ratio of ZSM-5 to mordenite is about 2:1 by weight.

The first zeolite preferably has a crystalline particulate size between approximately 0.45 microns and approximately 400 microns, where approximately 53.4% by volume of the first zeolite has a crystalline particulate size between approximately 1 micron and approximately 10 microns, and approximately 19.1% by volume of the first zeolite has a crystalline particulate size between approximately 10 microns and approximately 20 microns. The second zeolite preferably has a crystalline particulate size between approximately 0.45 microns and approximately 80 microns, where approximately 62.2% by volume of the second zeolite has a crystalline particulate size between approximately 1 micron and approximately 10 microns, and approximately 17.6% by volume of the second zeolite has a crystalline particulate size between approximately 10 microns and approximately 20 microns.

A refractory binder or matrix is optionally utilized to facilitate fabrication of the catalyst, to provide strength, and to reduce fabrication costs. The binder should be uniform in composition and relatively refractory to the conditions used in the process. Suitable binders include inorganic oxides, such as one or more of alumina, magnesia, zirconia, chromia, titania, boria, phosphate, zinc oxide and silica. Alumina is a preferred binder. The two different zeolites are mixed with the alumina binder in dry powdered form to yield a homogeneous mixture, thus to ensure homogeneous composition of the extrudates formed.

With reference to the hydrocarbon conversion process, the aromatic feed stream is preferably toluene and may include alkylaromatic hydrocarbons in the carbon number range of $C_9$ to $C_{11+}$, such as propylbenzenes, methylethylbenzenes, tetramethylbenzenes, butylbenzenes, dimethylethylbenzenes, diethylbenzenes, methylpropylbenzenes, or mixtures thereof. The aromatic feed stream allows for effective disproportionation of toluene into xylenes. The feed stream is preferably reacted in the vapor phase in the presence of hydrogen. The hydrogen is associated with the feed stream and recycled hydrocarbons, with hydrogen being provided at approximately 0.1 moles of hydrogen per mole of toluene to approximately 10.0 moles of hydrogen per mole of toluene.

Figure 2:
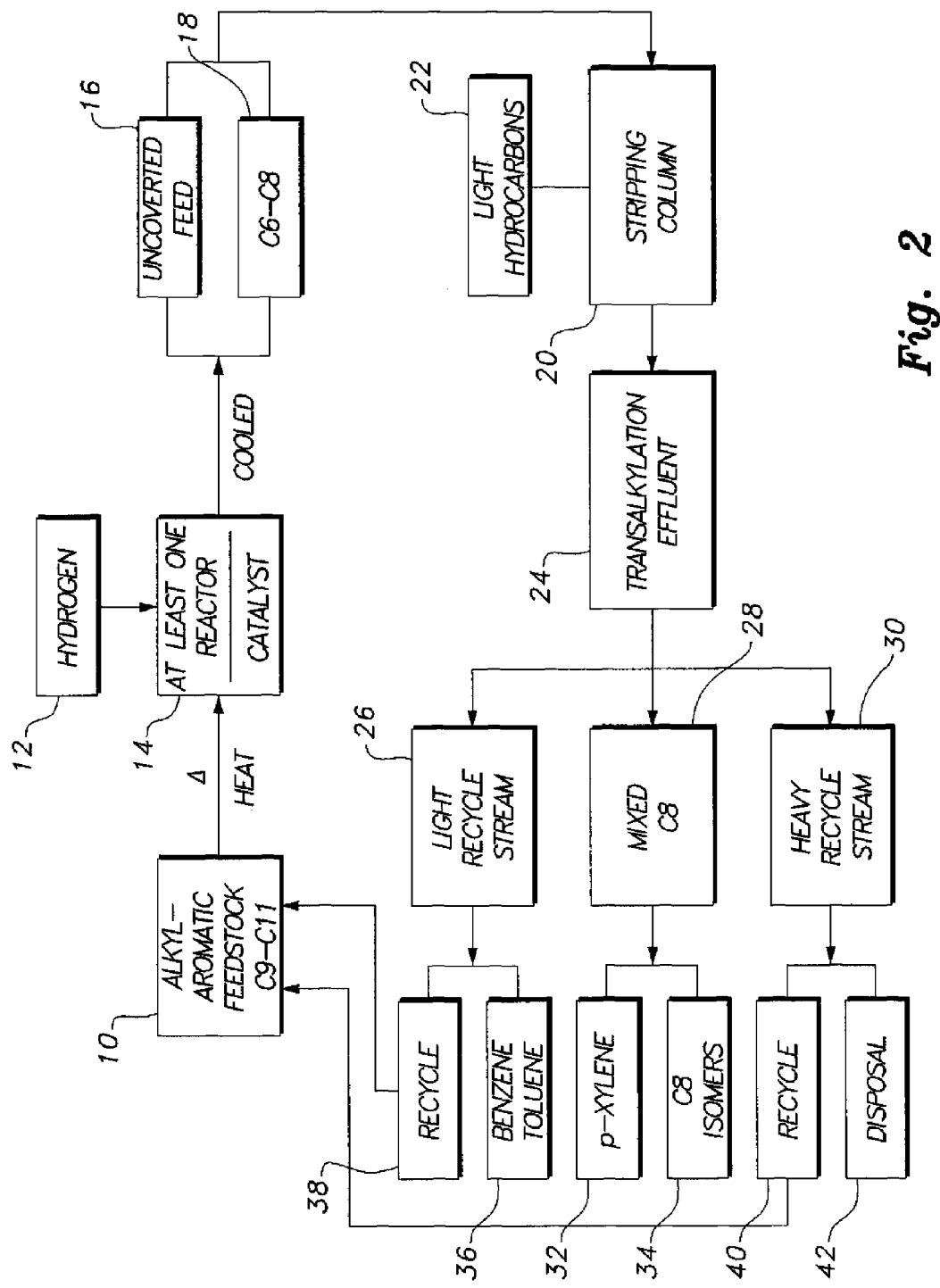
FIG. 2 is a block diagram showing a process for using the multiple zeolite catalyst according to the present invention for converting $C_{9+}$ alkylaromatic feedstock into BTX.

Referring to FIG. 2, the heavy aromatics feed stream 10, characterized by $C_{9+}$ aromatics, permits effective transalkylation of light aromatics such as benzene and toluene with the heavier $C_{9+}$ aromatics to yield additional $C_8$ aromatics that are preferably xylenes. The heavy aromatics stream 10 preferably comprises at least about 95 wt. % total aromatics, and may be derived from the same or different known refinery and petrochemical processes, and may be recycled from the separation of the product from transalkylation.

The feed stream is preferably transalkylated in the vapor phase and in the presence of hydrogen. The hydrogen 12 is associated with the feed stream 10 and recycled hydrocarbons in an amount from about 0.1 moles hydrogen per mole of alkylaromatics up to ten moles per mole of alkylaromatics. This ratio, of hydrogen to alkylaromatics is also referred to as the hydrogen-to-hydrocarbon ratio. The transalkylation reaction preferably yields a product having mixed xylene content, and also comprises toluene and benzene.

The feed to a transalkylation reaction zone usually is heated, first by indirect heat exchange against the effluent of the reaction zone, and then is heated to reaction temperature. The feed then is passed through a reaction zone, which may comprise one or more individual reactors 14. The use of a single reaction vessel having a fixed cylindrical bed of catalyst is preferred, but other reaction configurations utilizing moving beds of catalyst or radial-flow reactors may be employed, if desired. Passage of the combined feed through the reaction zone results in the production of an effluent stream comprising unconverted feed 16 and product hydrocarbons 18. This effluent is normally cooled by indirect heat exchange against the stream entering the reaction zone and then further cooled through the use of air or cooling water. The effluent may be passed into a stripping column 20 in which substantially all $C_5$ and lighter hydrocarbons present in the effluent are concentrated into an overhead stream 22 and removed from the process. An aromatics-rich stream is recovered as net stripper bottom, which is referred to herein as the transalkylation effluent 24.

To produce the transalkylation reaction, the process incorporates a transalkylation catalyst in at least one zone, but no limitation is intended in regard to a specific catalyst, other than such catalyst must possess a solid-acid component and a metal component. The heavier aromatic compounds will readily undergo conversion into lighter aromatics, such as toluene and xylenes. The conditions employed in the transalkylation zone normally include a temperature of from about 200° C. to about 540° C. The transalkylation zone is operated at moderately elevated pressures, broadly ranging from about 1.0 MPa to about 5.0 MPa. The transalkylation reaction can be effected over a wide range of space velocities. Liquid hourly space velocity (LHSV) is in the range of from about 1.0 to about 5.0 $hr^{-1}$.

The transalkylation effluent is separated into a light recycle stream 26, a mixed $C_8$ aromatics product 28, and a heavy recycle stream 30. The mixed $C_8$ aromatics product can be sent for recovery of p-xylene 32 and other valuable isomers 34. The light recycle stream may be diverted to other uses, such as to benzene and toluene recovery 36, but alternatively is recycled partially to the transalkylation zone. The heavy recycle stream 30 contains substantially all of the $C_9$ and heavier aromatics and may be partially or totally recycled 40 to the transalkylation reaction zone, or removed from the process for disposal 42 or other processing.

The multiple zeolite catalyst is also particularly useful in performing toluene disproportionation. The multiple zeolite catalyst contacts a toluene stream to perform the disproportionation. The disproportionation reaction preferably occurs at a temperature between approximately 200° C. and approximately 500° C. (more preferably, about 275° C. to 350° C., a pressure between 10-30 bar, and at a liquid hourly space velocity between approximately 1.0 $hr^{-1}$ and approximately 5.0 $hr^{-1}$ (more preferably, between 1.5 and 3.0 $hr^{-1}$, and the toluene stream preferably has a hydrogen to hydrocarbon ratio of about 2:1. The multiple zeolite catalyst acts as a solid acid catalyst in the toluene disproportionation reaction, thus producing toluene conversion and higher xylene yields at lower temperatures than in conventional toluene disproportionation processes.

The disproportionation reaction preferably yields a product having mixed xylene content, and also comprises benzene and some C9 aromatics. The feed to the disproportionation reaction zone is preferably first heated by indirect heat exchange against the effluent of the reaction zone, and then is heated to reaction temperature. The feed is then passed through a reaction zone, which may include one or more individual reactors. The use of a single reaction vessel having a fixed cylindrical bed of catalyst is preferred, but other reaction configurations utilizing moving beds of catalyst or radial-flow reactors may be employed, if desired. Passage of the combined feed through the reaction zone results in the production of an effluent stream consisting of unconverted feed and hydrocarbon products.

To produce the disproportionation reaction, the process incorporates the multiple zeolite disproportionation catalyst in at least one zone. The aromatic compound then undergoes conversion into aromatics, such as xylenes and benzene. The disproportionation effluent is separated into a light recycle stream, a mixed $C_8$ aromatics product, and a heavy recycle stream. The mixed $C_8$ aromatics product can be sent for recovery of p-xylene and other valuable isomers. The light recycle stream may be diverted to other uses, such as to benzene and toluene recovery, but alternatively is recycled partially to the disproportionation zone. The heavy recycle stream contains substantially all of the $C_9$ and heavier aromatics and may be partially or totally recycled to the disproportionation reaction zone, or removed from the process for disposal or further processing.

The catalysts were tested for toluene disproportionation reaction in a pilot plant using pure toluene (99.9% pure) to demonstrate effectiveness of the catalysts for conversion of toluene and production to xylenes. The catalytic test consisted of loading a vertical reactor with a set quantity of the catalyst and contacting the feed at approximately 1.0 to 5.0 MPa (10 bar to 50 bar) under a reaction temperature of approximately 200° C. to 500° C., at a space velocity (LHSV) of approximately 1.0 to 5.0 $hr^{-1}$ and hydrogen to hydrocarbon ratio ($H_2$/HC) of 2.0. Before contacting the catalyst with the feed, the catalyst was reduced under pressurized hydrogen gas at 400° C. Various feed conversion levels and xylene yields were obtained at different temperatures using different catalysts. The yield of xylenes was obtained from the percent of xylenes (sum of m-xylene, p-xylene and o-xylene) found in the reaction products. Total percent toluene conversion was calculated as: Toluene conversion percent=100×[(Toluene wt % in the feed)−(Toluene wt % in the product)]/(Toluene wt % in the feed).

EXAMPLE

For comparison purposes, an exemplary multiple zeolite catalyst and method of using the same for toluene disproportionation according to the present invention, designated as Catalyst A, was tested against four reference catalysts, designated Catalyst B, Catalyst C, Catalyst D and Catalyst E. Catalyst B, Catalyst C, Catalyst D and Catalyst E each have a single zeolite component. Catalyst A and Catalyst B each have two zeolite components and a single metal component, the difference being that Catalyst A has a ZSM-5:mordenite ratio is 2:1 by weight and Catalyst B has a ZSM-5:mordenite ratio of 1:2 by weight. It will be understood that the composition of Catalyst A is an exemplary embodiment only, not intended to limit the general description of the multiple zeolite catalyst of the multiple zeolite catalyst provided above.

Preparation of Catalyst A

One part of alumina binder (Cataloid AP-3, obtained from CCIC, Japan) in dry powder form was dispersed in deionized water for 30 minutes to prepare a homogenously dispersed alumina. A dry mixture of one part of uncalcined and untreated mordenite zeolite (HSZ-690HOA Tosoh) having a silica-to-alumina ratio of 240 and two parts of uncalcined and untreated ZSM-5 (CT-405, obtained from CATAL, UK) having a silica-to-alumina ratio of 30 was added to the dispersed alumina. The wet mixture of alumina, mordenite and ZSM-5, was thoroughly mixed into a homogeneous paste that was passed through a process of kneading, thus resulting into a thick kneaded material having enough water content to produce stable and strong extrudates. The kneaded material was converted into extrudates using a 1.5 mm diameter sieve connected a steel cylinder and piston assembly. Suitable pressure was applied during the extrudate formation process. The extrudates were dried and calcined. The composition of the extrudates was in weight ratio as follows: alumina:ZSM-5:mordenite (1:2:1). A solution of 0.84 g of hexaammonium heptamolybdate tetrahydrate was prepared in a predetermined amount of deionized water, enough to wet the extrudates. The solution was applied dropwise on 15 grams of extrudates, which were spread in a glass dish to ensure that all the extrudates were wetted with the Mo solution and to achieve 3% Mo on the extrudates. The extrudates were dried at room temperature overnight, then dried in an air circulated oven at 120° C., and then calcined in a furnace kept at 500° C.

Preparation of Catalyst B

Alumina binder (Cataloid AP-3, obtained from CCIC, Japan) in dry powder form was dispersed in deionized water for 30 minutes to prepare a homogenously dispersed alumina. The alumina binder forms one part of the mixture. Uncalcined and untreated mordenite zeolite (HSZ-690HOA Tosoh) having a silica to alumina ratio of 240, was added in powder form to the slurry of alumina in water (forming two parts of the mixture), and then uncalcined and untreated ZSM-5 (CT-405, obtained from CATAL, UK) having a silica to alumina ratio of 30 was added in powder form to the slurry (in a proportion of one part). Then, the total mixture was thoroughly mixed into a homogeneous paste that was passed through a process of kneading, thus resulting into a thick, kneaded material having enough water content to produce stable and strong extrudates. The kneaded material was converted into extrudates using 1.5 mm diameter sieve connected to a steel cylinder and piston assembly. Suitable pressure was applied during the extrusion process. The extrudates were dried and calcined. The composition of the extrudates was in weight ratio as follows: alumina:ZSM-5:mordenite (1:1:2).

Based on the wettability test, a solution of 0.84 g of hexaammonium heptamolybdate tetrahydrate was prepared in 12 g of deionized water. The solution was applied dropwise on the extrudates, which were spread in a glass dish, to ensure that all the extrudates were impregnated with the Mo solution to achieve 3% Mo on the extrudates. The extrudates were dried at room temperature overnight, then dried in air-circulated oven at 120° C., and then calcined in a furnace kept at 500° C.

Preparation of Catalyst C

Alumina binder (Cataloid AP-3, obtained from CCIC, Japan) in dry powder form was dispersed in deionized water for 30 minutes to prepare a homogenously dispersed alumina. The alumina binder forms one part of the mixture. A dry powder mixture of three parts of uncalcined and untreated ZSM-5 (CT-405, obtained from CATAL, UK) having a silica to alumina ratio of 30 was added in powder form to the dispersed alumina. Then, the mixture of alumina and ZSM-5 was thoroughly mixed into a homogeneous paste that was passed through a process of kneading, thus resulting into a thick, kneaded material having enough water content to produce stable and strong extrudates. The kneaded material was converted into extrudates using 1.5 mm diameter sieve connected to a steel cylinder and piston assembly. Suitable pressure was applied during the extrusion process. The extrudates were dried and calcined. The composition of the extrudates was in weight ratio as follows: AP-3:ZSM-5(1:3).

Based on the wettability test, a solution of 0.84 g of hexaammonium heptamolybdate tetrahydrate was prepared in enough deionized water to wet the extrudates. The solution was applied dropwise on 15 g of the extrudates, which were spread in a glass dish, to ensure that all the extrudates were impregnated with the Mo solution to achieve 3% Mo on the extrudates. The extrudates were dried at room temperature overnight, then dried in air-circulated oven at 120° C., and then calcined in a furnace kept at 500° C.

Preparation of Catalyst D

Alumina binder (Cataloid AP-3, obtained from CCIC, Japan) in dry powder form was dispersed in deionized water for 30 minutes to prepare a homogenously dispersed alumina. The alumina binder forms one part of the mixture. A dry powder mixture of three parts of uncalcined and untreated ZSM-5 (CT-405, obtained from CATAL, UK) having a silica to alumina ratio of 30 was added in powder form to the dispersed alumina. The wet mixture of alumina and ZSM-5 was thoroughly mixed into a homogeneous paste that was passed through a process of kneading, thus resulting into a thick, kneaded material having enough water content to produce stable and strong extrudates. The kneaded material was converted into extrudates using 1.5 mm diameter sieve connected to a steel cylinder and piston assembly. Suitable pressure was applied during the extrusion process. The extrudates were dried and calcined. The composition of the extrudates was in weight ratio as follows: AP-3:ZSM-5(1:3). No molybdenum was added. The extrudates were dried at room temperature overnight and then calcined in a furnace kept at 500° C.

Preparation of Catalyst E

In Catalyst E, the extrudates of Catalyst D were modified using a phosphorus containing compound in order to increase the para-selectivity for xylenes. 1.8 grams of ammonium hydrogen phosphate [$(NH_4)_2HPO_4$] was dissolved in 5.0 ml of distilled water and mixed well to produce a homogeneous solution. The solution was then added dropwise to 5.0 grams of AC-52 extrudates spread in a glass dish. The extrudates were wetted by the solution to have phosphorus impregnation. The extrudates were dried at room temperature, then dried in an air circulated oven at 120° C., and then calcined in a furnace for three hours at 500° C.

Catalyst A was tested for disproportionation reaction in a pilot plant using a pure toluene feed (99.9% purity) to demonstrate effectiveness of the catalysts for toluene conversion and production of xylenes. Generally, the samples may be tested by the steps of: (a) reducing the catalyst under hydrogen gas flow of 100 to 200 ml/min at a pressure 0f 10-30 bar and a temperature of 400° C. to 500° C. for about 3 hours; (b) contacting the catalyst with a pure toluene feed (preferably 99.5% pure) at a flow of 10.5 ml/hour and hydrogen gas (preferably 99.9% pure) at a flow of 100 to 200 ml/min in a reaction zone located in the middle of the reactor tube at a pressure of 10-30 bar at temperature of 275 to 350° C. for about 3 hours at a space velocity of 1.5 to 3.0 $hr^{-1}$ and at a hydrogen-to-hydrocarbon ratio of 2 in a single pass through the reactor; stripping lighter hydrocarbons from the product in a gas-liquid separator; and analyzing the heavier product in a hydrocarbon specific analyzer. In particular, the catalytic test consisted of loading a vertical reactor with 7.0 ml of the catalyst extrudates in the middle of the reactor, together with inert alumina balls in lower and upper parts of the reactor. The total volume of the reactor was 50 ml.

The catalyst was activated and reduced under 122 ml/min flow of pure hydrogen gas at 400° C. at 30 bar pressure (3.0 MPa), and was kept at these conditions for three hours. Then, the temperature of the reactor was reduced to 275° C. and the flow of the toluene feed was started and set at 10.5 ml/h, with a hydrogen-to-hydrocarbon ratio of 2.0. The reaction was allowed to run for 24 hours at this temperature before collection of the sample.

The reaction product was separated in a gas-liquid separator. Both gas and liquid samples were collected and analyzed. The temperature was then changed to 300° C., and the reaction was conducted again with fresh toluene feed for another 24 hours before collecting the gas and liquid samples.

In this manner, product samples were collected at 275° C., 300° C., 325° C., 350° C. and 375° C. reaction temperatures. Various feed conversion levels were obtained at different temperatures and different space velocities, and the results show high and moderate conversion of toluene. The liquid reaction products were analyzed using a PIONA Analyzer based on Shimadzu gas chromatograph GC-2010 and Shimadzu auto-injector AOC-20i. The PIONA Analyzer is equipped with an FID detector and autosampler. The hydrocarbon separation was carried out on a 50 meter long and 0.15 mm diameter BP1PONA-M50-050 column under temperature programmed conditions. The components were separated according to their boiling points. The components were identified using a calibration that was accomplished using a standard hydrocarbon mixture sample having the components of known composition. Table 1 (below) presents toluene conversion and xylene yield results obtained for Catalyst A:

TABLE 1

Results for Catalyst A

|  | Catalyst A | Catalyst A | Catalyst A | Catalyst A | Catalyst A |
| --- | --- | --- | --- | --- | --- |
| Reaction Temperature, ° C. | 275 | 300 | 325 | 350 | 375 |
| Toluene Conversion, mol % | 10.6 | 30.3 | 44.3 | 53.6 | 56.1 |
| Xylenes yield, mol % | 4.4 | 13.8 | 18.6 | 19.1 | 19.3 |
| m-Xylene, yield, mol % | 2.5 | 7.9 | 10.3 | 10.4 | 10.4 |
| p-Xylene, yield, mol % | 1.0 | 3.0 | 4.2 | 4.4 | 4.5 |
| o-Xylene, yield, mol % | 0.9 | 2.9 | 4.1 | 4.3 | 4.4 |

Table 2 shows the toluene conversion and xylene yield results for Catalyst B. Table 2 illustrates the production of xylenes from the disproportionation reaction of toluene using Catalyst B following the same procedure described above, with the batch reactor charged with 7.0 ml of Catalyst B and with the performance being monitored over the temperatures 275° C., 300° C., 325° C., and 350° C.:

TABLE 2

Results for Catalyst B

|  | Catalyst of B | Catalyst of B | Catalyst of B | Catalyst of B |
|---|---|---|---|---|
| Reaction Temperature, ° C. | 275 | 300 | 325 | 350 |
| Toluene Conversion, mol % | 2.1 | 6.3 | 15.1 | 32.9 |
| Xylenes yield, mol % | 1.0 | 3.1 | 7.4 | 14.6 |
| m-Xylene, yield, mol % | 0.5 | 1.6 | 4.1 | 8.0 |
| p-Xylene, yield, mol % | 0.3 | 0.9 | 1.7 | 3.4 |
| o-Xylene, yield, mol % | 0.2 | 0.6 | 1.6 | 3.2 |

Table 3 shows the toluene conversion and xylene yield results for Catalyst C. Table 3 illustrates the production of xylenes from the disproportionation reaction of toluene using Catalyst C following the same procedure described above, with the batch reactor charged with 7.0 ml of Catalyst C and with the performance being monitored over the temperatures 350° C. and 375° C.:

TABLE 3

Results for Catalyst C

|  | Catalyst of C | Catalyst of C |
|---|---|---|
| Reaction Temperature, ° C. | 350 | 375 |
| Toluene Conversion, mol % | 26.3 | 34.2 |
| Xylenes yield, mol % | 8.7 | 13.3 |
| m-Xylene, yield, mol % | 4.5 | 7.2 |
| p-Xylene, yield, mol % | 2.2 | 3.2 |
| o-Xylene, yield, mol % | 2.0 | 2.9 |

Table 4 shows the toluene conversion and xylene yield results for Catalyst D. Table 4 illustrates the production of xylenes from the disproportionation reaction of toluene using Catalyst D following the same procedure described above, with the batch reactor charged with 7.0 ml of Catalyst D and with the performance being monitored over the temperatures 350° C. and 375° C.:

TABLE 4

Results for Catalyst D

|  | Catalyst D | Catalyst D |
|---|---|---|
| Reaction Temperature, ° C. | 350 | 375 |
| Toluene Conversion, mol % | 28.5 | 34.7 |
| Xylenes yield, mol % | 13.0 | 14.9 |
| m-Xylene, yield, mol % | 7.3 | 8.1 |
| p-Xylene, yield, mol % | 2.9 | 3.5 |
| o-Xylene, yield, mol % | 2.8 | 3.3 |

Table 5 shows the toluene conversion and xylene yield results for Catalyst E. Table 5 illustrates the production of xylenes from the disproportionation reaction of toluene using Catalyst E following the same procedure described above, with the batch reactor charged with 7.0 ml of Catalyst E and with the performance being monitored over the temperatures 350° C. and 375° C.:

TABLE 5

Results for Catalyst E

|  | Catalyst E | Catalyst E |
|---|---|---|
| Reaction Temperature, ° C. | 350 | 375 |
| Toluene Conversion, mol % | 26.9 | 32.6 |
| Xylenes yield, mol % | 12.1 | 12.7 |
| m-Xylene, yield, mol % | 6.6 | 6.9 |
| p-Xylene, yield, mol % | 2.9 | 3.1 |
| o-Xylene, yield, mol % | 2.6 | 2.7 |

Comparing the percent conversion of toluene feed at reaction conditions (350° C., 1.5 LHSV and 30 bar hydrogen pressure) obtained using Catalyst A and Catalysts B-E, it is evident that Catalyst A according to the present invention shows higher percent toluene conversion as compared to Catalysts B-E. Similarly, the comparison of the xylene yield obtained using the Catalyst A at reaction conditions (350° C. and 1.5 LHSV, 30 bar hydrogen pressure) shows a higher xylene yield for Catalyst A than Catalysts B-E.

Likewise, evaluating and comparing the percent conversion of toluene at the reaction conditions (375° C., 1.5 LHSV and 30 bar hydrogen pressure) obtained by utilizing Catalyst A and Catalysts C-E, it is evident that Catalyst A shows higher percent toluene conversion as compared to the Catalysts C-E. Similarly, the comparison of the xylene yield obtained using Catalyst A at reaction conditions (375° C. and 1.5 LHSV, 30 bar hydrogen pressure) shows a higher xylene yield for Catalyst A than Catalysts C-E.

It is to be understood that the present invention is not limited to the embodiments described above, but encompasses any and all embodiments within the scope of the following claims.

I claim:

1. A method of converting toluene to xylene, comprising the steps of:
    reducing a multiple zeolite catalyst with hydrogen gas at about 400° C., the multiple zeolite catalyst consisting of:
        mordenite having a silica to alumina ratio of about 240 to 1;
        ZSM-5 having a silica to alumina ratio of about 30 to 1;
        alumina binder, the mordenite and the ZSM-5 forming a homogenous mixture with the binder; and
        molybdenum added to the mixture of the alumina binder, the mordenite, and the ZSM-5, the molybdenum forming about 3 wt. % of the catalyst;
    contacting a feed consisting essentially of toluene with the reduced multiple zeolite catalyst and hydrogen in a reactor at a pressure between 10 to 30 bar, a temperature of 275° C. to 350° C., a space velocity of 1.5 to 3.0 hr$^{-1}$, and a hydrogen to hydrocarbon ratio of 2:1 to produce an effluent in a single-stage process;
    stripping C5 and lighter hydrocarbons and stripping unreacted feed from the effluent; and
    collecting a mixture of xylene isomers from the effluent.

2. The method of converting toluene to xylene according to claim 1, wherein the multiple zeolite catalyst contains ZSM-5 and mordenite in a ratio of 2:1 by weight.

3. The method of converting toluene to xylene according to claim 1, wherein the feed consists of 99.5% pure toluene.

4. The method of converting toluene to xylene according to claim 1, wherein said step of reducing the multiple zeolite catalyst with hydrogen gas comprises reducing the multiple zeolite catalyst in a stream of hydrogen gas at a gas flow rate of 100 too 200 ml/min for about three hours.

5. The method of converting toluene to xylene according to claim 4, wherein said step of reducing the multiple zeolite catalyst with hydrogen gas is performed at a pressure between 10 and 30 bar.

6. The method of converting toluene to xylene according to claim 1, wherein said step of contacting the feed with the multiple zeolite catalyst comprises feeding the toluene over the multiple zeolite catalyst at a flow rate of about 10.5 ml/hour.

7. The method of converting toluene to xylene according to claim 1, wherein said multiple zeolite catalyst is in the form of extrudates.

8. The method of converting toluene to xylene according to claim 1, wherein the multiple zeolite catalyst contains alumina, ZSM-5, and mordenite in a ratio of 1:2:1 by weight.

* * * * *